United States Patent
Wachi et al.

(10) Patent No.: US 7,033,802 B1
(45) Date of Patent: Apr. 25, 2006

(54) PENICILLIN BINDING PROTEIN GENE AND PROCESS FOR PRODUCING L-GLUTAMIC ACID

(75) Inventors: Masaaki Wachi, Machida (JP); Kazuo Nagai, Tokyo (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/623,596

(22) PCT Filed: Mar. 5, 1999

(86) PCT No.: PCT/JP99/01084

§ 371 (c)(1),
(2), (4) Date: Sep. 5, 2000

(87) PCT Pub. No.: WO99/45131

PCT Pub. Date: Sep. 10, 1999

(30) Foreign Application Priority Data

Mar. 6, 1998 (JP) ............................. 10-055608

(51) Int. Cl.
*C12P 13/14* (2006.01)
(52) U.S. Cl. .............. 435/110; 435/320.1; 435/252.32; 435/252.33; 536/23.1; 536/23.2
(58) Field of Classification Search ................ 435/110, 435/320.1, 252.33, 252.322, 252.3; 536/23.1, 536/23.2, 23.7
See application file for complete search history.

(56) References Cited

U.S. PATENT DOCUMENTS

| 3,080,297 A | 3/1963 | Phillips et al. |
| 5,929,221 A | 7/1999 | Kimura et al. |
| 5,977,331 A | 11/1999 | Asakura et al. |

FOREIGN PATENT DOCUMENTS

| EP | 0 752 472 | 1/1997 |
| EP | 0 771 879 | 5/1997 |
| EP | 0 780 477 | 6/1997 |
| WO | WO 95/23224 | 8/1995 |
| WO | WO 95/34672 | 12/1995 |

OTHER PUBLICATIONS

Cole et al. GenBank Accession No. Z95388. "*Mycobacterium tuberculosis* H37Rv complete genome, segment 96/162" created May 14, 1997.*
Cole et al. GenBank Accession No. B70886 "probably penicillin binding protein—*Mycobacterium tuberculosis* (strain H37RV)" created Jul. 17, 1998.*
T.D. Nunheimer, et al., Applied Microbiology, vol. 20, No. 2, pp. 215-217, "Product Inhibition of the Fermentative Formation of Glutamic Acid", Aug. 1970.
Brian G. Spratt, Proc. Nat. Acad. Sci. USA, vol. 72, No. 8, pp. 2999-3003, "Distinct Penicillin Binding Proteins Involved in the Division, Elongation, and Shape of *Escherichia coli* K12", Aug. 1975.
Brian G. Spratt, Journal of Bacteriology, vol. 131, No. 1, pp. 293-305, "Temperature-Sensitive Cell Division Mutants of *Escherchia coli* With Thermolabile Penicillin-Binding Proteins", Jul. 1977.
Masataka Nakamura, et al., Mol. Gen. Genet., vol. 191, pp. 1-9, "On the Process of Cellular Division in *Escherichia coli*: Nucleotide Sequence of the Gene for Penicillin-Binding Protein 3", 1983.
G. Laible, et al., Molecular Microbiology, vol. 3, No. 10, pp. 1337-1348, "Nucleotide Sequences of the PBPX Genes Encoding the Penicillin-Binding Proteins 2X From *Streptococcus pneumoniae* R6 and a Cefotaxime-Resistant Mutant, C506", 1989.
M.L. Valenski, et al., "The Product of the Fimi Gene is Necessary for *Escherichia coli* Type 1 Pilus Biosynthesis", Journal of Bacteriology, vol. 185, No. 16, Aug. 2003, pp. 5007-5011.
Database Online !, Database Accession No. 006214, pp. 1-2, 4, "Description and Origin of the Protein" Jul. 1, 1997.

* cited by examiner

*Primary Examiner*—Kathleen Kerr
(74) *Attorney, Agent, or Firm*—Oblon, Spivak, McClelland, Maier & Neustadt, P.C.

(57) ABSTRACT

The present invention relates to a penicillin binding protein, DNA encoding the protein and methods of producing L-glutamic acid in *Corynebacterium glutamicum*, which has a reduction of penicillin binding protein activity.

21 Claims, 1 Drawing Sheet

SEQUENCE LISTING

```
<160> NUMBER OF SEQ ID NOS: 6

<210> SEQ ID NO 1
<211> LENGTH: 5345
<212> TYPE: DNA
<213> ORGANISM: Brevibacterium lactofermentum
<220> FEATURE:
<221> NAME/KEY: CDS
<222> LOCATION: (881)..(2623)
<221> NAME/KEY: CDS
<222> LOCATION: (2790)..(4454)
<221> NAME/KEY: CDS
<222> LOCATION: (4467)..(5345)

<400> SEQUENCE: 1
aagcttcggg gagggcgcg  tcgataagca  cgcaacctcg  tcgtgacatg  gcgccggaaa      60
ggaaacaacc  cgggccctgg  tgaaccctgg  cgtgcagcaa  cgcgtaattg  atgcagcaca     120
agctgggctc  tcagcaggtt  atgtcggtgc  gtggtcgccg  cgttgaggca  aaacgtgctg     180
atcctaaggt  gatccagctg  tctgtgctgg  tggttatcct  gctgtgcgtt  ggtgttggcg     240
cgaccatggg  tctgtccgga  acgtctacac  agcagacttt  ccagttgcag  gaacttcagg     300
caactgaaac  ggatttgagc  aatcgcattg  agtctctcaa  ccgagatgtg  gaagatgctc     360
gctcagcagc  aaccttggca  gcgaatgcta  cggagatggg  cttggtatcc  ccagtggaac     420
ctggcgtgct  cgcagtgcag  gaaaacggtg  atgttgtgga  ggagcgcgaa  caaatccaga     480
gacacgccct  atagttgaca  tcaatggaca  acagacccga  ccaaatcggg  catcaagcaa     540
ccctgacgag  actaacgcat  actgaaaacc  tccaggcgat  tccacaagaa  gcagcagctc     600
cgccgtatca  gaccaacact  gttccttatg  ctgcaaccac  cggacaagca  ggtggcgcag     660
ggcagtgact  ttccccagca  atggcagaag  tcggggcgag  cgtgcgggac  gtgaagatac     720
gtcccgccgt  tcggcgtatc  aggacgaaag  cagaagagcc  gctagagagc  gcgaacttac     780
gcgacgcagc  ggtaaagcta  aaggcgtaaa  ccaagaagaa  ggagtgacct  accggcctaa     840
atcttcaacc  cagggcggcg  cacgcaagcg  acgtgtgaac  atg gtt acc cgt atc         895
                                                 Met Val Thr Arg Ile
                                                  1               5 gca ttg gtc atc gct ggc gta ctg atc att cgc ctc ggc tgg gtc caa              943
Ala Leu Val Ile Ala Gly Val Leu Ile Ile Arg Leu Gly Trp Val Gln
              10                  15                  20 gtt gtc tgg gga cca gaa ctg tcc ctc aat gct tcg gaa cag cgc acc              991
Val Val Trp Gly Pro Glu Leu Ser Leu Asn Ala Ser Glu Gln Arg Thr
          25                  30                  35 cgc gtg tac gta gat cct gca cgc cgt gga acc atc gtg gac cgc gaa             1039
Arg Val Tyr Val Asp Pro Ala Arg Arg Gly Thr Ile Val Asp Arg Glu
      40                  45                  50
```

```
gga aac cag atg gcg tac acg atg cag gca cgt tcg ctg acg gtt tct    1087
Gly Asn Gln Met Ala Tyr Thr Met Gln Ala Arg Ser Leu Thr Val Ser
    55                  60                  65 ccg aac atc atg cgt gag gaa tta aag acc gga act gat ctg gcc ttg    1135
Pro Asn Ile Met Arg Glu Glu Leu Lys Thr Gly Thr Asp Leu Ala Leu
70                  75                  80                  85 cgt ttg gcg gct gaa gaa acc gat ccg gaa aac gtg gcc agc tat gtg    1183
Arg Leu Ala Ala Glu Glu Thr Asp Pro Glu Asn Val Ala Ser Tyr Val
                90                  95                 100 acc atc gaa gaa ggc aac gcg tat gtt ttt gcg tct gaa gaa cag cgc    1231
Thr Ile Glu Glu Gly Asn Ala Tyr Val Phe Ala Ser Glu Glu Gln Arg
            105                 110                 115 gaa acc att ctg tcc gac aag gta gaa gag cgt att caa agc att gcg    1279
Glu Thr Ile Leu Ser Asp Lys Val Glu Glu Arg Ile Gln Ser Ile Ala
        120                 125                 130 gat cgg atc cct gag atc atc aaa tcc cat gac caa gat gtc act gga    1327
Asp Arg Ile Pro Glu Ile Ile Lys Ser His Asp Gln Asp Val Thr Gly
    135                 140                 145 att tcc tct gag gag atc ctg gac aag ctc aat gca gat agc cag tat    1375
Ile Ser Ser Glu Glu Ile Leu Asp Lys Leu Asn Ala Asp Ser Gln Tyr
150                 155                 160                 165 gag gtg ctc gtc cgc aat gtt gat ccc gat gta gcg tca gaa atc acc    1423
Glu Val Leu Val Arg Asn Val Asp Pro Asp Val Ala Ser Glu Ile Thr
                170                 175                 180 gat gag atg ccc agc gtc gca gct gat cat caa gac atc cgc caa tac    1471
Asp Glu Met Pro Ser Val Ala Ala Asp His Gln Asp Ile Arg Gln Tyr
            185                 190                 195 cca aac ggc gcg att ggt gaa aac atc atc ggt cga atc agc atg gac    1519
Pro Asn Gly Ala Ile Gly Glu Asn Ile Ile Gly Arg Ile Ser Met Asp
        200                 205                 210 ggc gaa ggc cag ttc ggc ttt gag gct tcc aac gat tcc ctg ttg gca    1567
Gly Glu Gly Gln Phe Gly Phe Glu Ala Ser Asn Asp Ser Leu Leu Ala
    215                 220                 225 gga aac aac ggt cgc tca acc cag gac atg tcc att ttg gga caa gca    1615
Gly Asn Asn Gly Arg Ser Thr Gln Asp Met Ser Ile Leu Gly Gln Ala
230                 235                 240                 245 atc ccg ggc acg ttg agg gat caa att cca gcc att gat ggt gcc agc    1663
Ile Pro Gly Thr Leu Arg Asp Gln Ile Pro Ala Ile Asp Gly Ala Ser
                250                 255                 260 gtt gaa ctc acc gtt gat ctg gat ctg caa acc tat gtg cag cag gca    1711
Val Glu Leu Thr Val Asp Leu Asp Leu Gln Thr Tyr Val Gln Gln Ala
            265                 270                 275 ttg gag cag gcg aaa gct aac tcc ggt gca gaa aac gcc tcc gct gtg    1759
Leu Glu Gln Ala Lys Ala Asn Ser Gly Ala Glu Asn Ala Ser Ala Val
        280                 285                 290 gtt ctt gat gcc gag acc gct gag gtt ttg gcg atg gca aac acc gat    1807
Val Leu Asp Ala Glu Thr Ala Glu Val Leu Ala Met Ala Asn Thr Asp
    295                 300                 305 acc atc aac ccc aac gaa gac acg gga aag cag att gag cag ggc aag    1855
Thr Ile Asn Pro Asn Glu Asp Thr Gly Lys Gln Ile Glu Gln Gly Lys
310                 315                 320                 325 agc ttt gac aat cct tct gtc acc cac ccc ttc gag cct ggt tct gta    1903
Ser Phe Asp Asn Pro Ser Val Thr His Pro Phe Glu Pro Gly Ser Val
                330                 335                 340 gcc aag gtg att act gca gca ggc gta att caa gac ggc ttg act act    1951
Ala Lys Val Ile Thr Ala Ala Gly Val Ile Gln Asp Gly Leu Thr Thr
            345                 350                 355 cca gat gaa gtg ttg cag gta ccg ggc agt att gaa atg gcc ggt gtt    1999
Pro Asp Glu Val Leu Gln Val Pro Gly Ser Ile Glu Met Ala Gly Val
        360                 365                 370
```

-continued

| | |
|---|---|
| tct gtc ggt gat gcg tgg gac cac ggt gtc gtt ccc tat acc act gca<br>Ser Val Gly Asp Ala Trp Asp His Gly Val Val Pro Tyr Thr Thr Ala<br>375                              380                        385 | 2047 |
| gga att ttt ggt aag tcc tcg aat gta ggc act ctg atg ctt gcg cac<br>Gly Ile Phe Gly Lys Ser Ser Asn Val Gly Thr Leu Met Leu Ala His<br>390                              395                        400              405 | 2095 |
| ggt ctt ggt gaa gat aaa ttt gct gat tac ctg gaa cga ttc ggt gtg<br>Gly Leu Gly Glu Asp Lys Phe Ala Asp Tyr Leu Glu Arg Phe Gly Val<br>                      410                        415                      420 | 2143 |
| gga cag tca acg ggt att gag ctt ccg agc gaa tcc caa ggc ctg ctg<br>Gly Gln Ser Thr Gly Ile Glu Leu Pro Ser Glu Ser Gln Gly Leu Leu<br>425                              430                        435 | 2191 |
| ccc gca cgt gag cag tgg tct ggc ggt act ttt gct aac ctg ccc atc<br>Pro Ala Arg Glu Gln Trp Ser Gly Gly Thr Phe Ala Asn Leu Pro Ile<br>            440                        445                        450 | 2239 |
| ggt cag ggt atg tcg atc acc acg ttg caa atg gct gga atc tac caa<br>Gly Gln Gly Met Ser Ile Thr Thr Leu Gln Met Ala Gly Ile Tyr Gln<br>455                              460                        465 | 2287 |
| gcc ttg gcc aac gat ggt gaa cgc att gaa ccg cgg atc atc aag agc<br>Ala Leu Ala Asn Asp Gly Glu Arg Ile Glu Pro Arg Ile Ile Lys Ser<br>470                              475                        480              485 | 2335 |
| gtg act gat tct gac gga aca gtc cta gag cag ccg gaa ccc gat aaa<br>Val Thr Asp Ser Asp Gly Thr Val Leu Glu Gln Pro Glu Pro Asp Lys<br>                      490                        495                      500 | 2383 |
| atc cag gtt gtc agc gct gaa gct gcc cgc acc acg gtg gat atg ttt<br>Ile Gln Val Val Ser Ala Glu Ala Ala Arg Thr Thr Val Asp Met Phe<br>505                              510                        515 | 2431 |
| agg tct gtc acc cag gtt gat cca ctt gga gtg cac aag gta ccg ctc<br>Arg Ser Val Thr Gln Val Asp Pro Leu Gly Val His Lys Val Pro Leu<br>            520                        525                        530 | 2479 |
| cag acg cct cca ttg agg gtt atc aaa tct cag gta aga cag gta cgg<br>Gln Thr Pro Pro Leu Arg Val Ile Lys Ser Gln Val Arg Gln Val Arg<br>535                              540                        545 | 2527 |
| cgc aaa aag ttg acc cca aca cgg gcg cgt act cta act cgc aat act<br>Arg Lys Lys Leu Thr Pro Thr Arg Ala Arg Thr Leu Thr Arg Asn Thr<br>550                              555                        560              565 | 2575 |
| gga tta cct tct cgg gta ttg cac ccg ctg atg atc ctc gat ttg ttg<br>Gly Leu Pro Ser Arg Val Leu His Pro Leu Met Ile Leu Asp Leu Leu<br>                      570                        575                      580 | 2623 |
| tagccatcat gcttgatgag ccagaacgcg gagtccacgg tggtggcggc caaaccgcag | 2683 |
| caccttttgtt caaagacatc gccacctggt tgctcaaccg cgacaacatc ccactgtctg | 2743 |
| cagccaccga accgatcatc cttcaagctc aataactcaa acagaa gtg tct ttt<br>                                                                                                    Val Ser Phe | 2798 |
| gta gaa ttt cat aat ctg aac ttt tgt ttg aac tct ttt cgg cat cac<br>Val Glu Phe His Asn Leu Asn Phe Cys Leu Asn Ser Phe Arg His His<br>585                              590                        595              600 | 2846 |
| cca cgt gcc gcg tcc gaa tta tta aca cct aga aac ctg tgg agg aga<br>Pro Arg Ala Ala Ser Glu Leu Leu Thr Pro Arg Asn Leu Trp Arg Arg<br>                      605                        610                      615 | 2894 |
| gaa aac cat ggc aac cac gtt gct gga cct cac caa act tat cga tgg<br>Glu Asn His Gly Asn His Val Ala Gly Pro His Gln Thr Tyr Arg Trp<br>                      620                        625                      630 | 2942 |
| cat cct caa ggg ctc tgc cag ggc gtt ccc gct cac gca gta ggg gaa<br>His Pro Gln Gly Leu Cys Gln Gly Val Pro Ala His Ala Val Gly Glu<br>                        635                        640                      645 | 2990 |
| caa gca atc gcg gct att ggt ctt gac tcc tcc agc ttg cct acc tcg<br>Gln Ala Ile Ala Ala Ile Gly Leu Asp Ser Ser Ser Leu Pro Thr Ser<br>650                              655                        660 | 3038 |

-continued

| | | |
|---|---|---|
| gac gct att ttt gct gca gtt cca gga acc cgc act cac ggc gca cag<br>Asp Ala Ile Phe Ala Ala Val Pro Gly Thr Arg Thr His Gly Ala Gln<br>665                    670                    675                    680 | 3086 |
| ttt gca ggt acg gat aac gct gcg aaa gct gtg gcc att ttg act gac<br>Phe Ala Gly Thr Asp Asn Ala Ala Lys Ala Val Ala Ile Leu Thr Asp<br>                    685                    690                    695 | 3134 |
| gca gct gga ctt gag gtg ctc aac gaa gca gga gag acc cgc cca atc<br>Ala Ala Gly Leu Glu Val Leu Asn Glu Ala Gly Glu Thr Arg Pro Ile<br>700                    705                    710 | 3182 |
| atc gtt gtt gat gat gtc cgc gca gta ctt ggc gca gca tca tca agc<br>Ile Val Val Asp Asp Val Arg Ala Val Leu Gly Ala Ala Ser Ser Ser<br>                    715                    720                    725 | 3230 |
| att tat ggc gat cct tca aaa gat ttc acg ctc att gga gtc act gga<br>Ile Tyr Gly Asp Pro Ser Lys Asp Phe Thr Leu Ile Gly Val Thr Gly<br>730                      735                    740 | 3278 |
| acc tca ggt aaa acc acc acc agc tac ctc ttg gaa aaa gga ctc atg<br>Thr Ser Gly Lys Thr Thr Thr Ser Tyr Leu Leu Glu Lys Gly Leu Met<br>745                    750                    755                    760 | 3326 |
| gag gca ggc cac aaa gtt ggt ttg atc ggc acc aca ggt aca cgt ata<br>Glu Ala Gly His Lys Val Gly Leu Ile Gly Thr Thr Gly Thr Arg Ile<br>                    765                    770                    775 | 3374 |
| gat ggg gaa gaa gta ccc acg aag ctc acc act cca gaa gcg ccg act<br>Asp Gly Glu Glu Val Pro Thr Lys Leu Thr Thr Pro Glu Ala Pro Thr<br>780                      785                    790 | 3422 |
| ctg cag gca ttg ttt gct cga atg cgc gat cac ggt gtc acc cac gtg<br>Leu Gln Ala Leu Phe Ala Arg Met Arg Asp His Gly Val Thr His Val<br>                    795                    800                    805 | 3470 |
| gtg atg gaa gta tcc agc cat gca ttg tca ttg ggc agg gtt gcg ggt<br>Val Met Glu Val Ser Ser His Ala Leu Ser Leu Gly Arg Val Ala Gly<br>810                      815                    820 | 3518 |
| tcc cac ttt gat gta gct gcg ttt acc aac ctg tcg cag gat cac ctt<br>Ser His Phe Asp Val Ala Ala Phe Thr Asn Leu Ser Gln Asp His Leu<br>825                    830                    835                    840 | 3566 |
| gat ttc cac ccc acc atg gat gat tac ttt gac gcg aag gca ttg ttc<br>Asp Phe His Pro Thr Met Asp Asp Tyr Phe Asp Ala Lys Ala Leu Phe<br>                    845                    850                    855 | 3614 |
| ttc cgc gca gat tct cca ctt gtg gct gac aaa cag gtc gtg tgc gtg<br>Phe Arg Ala Asp Ser Pro Leu Val Ala Asp Lys Gln Val Val Cys Val<br>860                      865                    870 | 3662 |
| gat gat tct tgg ggt cag cgc atg gcc agc gtg gca gcg gat gtg caa<br>Asp Asp Ser Trp Gly Gln Arg Met Ala Ser Val Ala Ala Asp Val Gln<br>                    875                    880                    885 | 3710 |
| aca gta tcc acc ctt ggg caa gaa gca gac ttc agc gct aca gat atc<br>Thr Val Ser Thr Leu Gly Gln Glu Ala Asp Phe Ser Ala Thr Asp Ile<br>890                      895                    900 | 3758 |
| aat gtc agc gac tct ggc gcc cag agt ttt aag atc aac gcc ccc tca<br>Asn Val Ser Asp Ser Gly Ala Gln Ser Phe Lys Ile Asn Ala Pro Ser<br>905                    910                    915                    920 | 3806 |
| aac cag tcc tac cag gtc gag cta gcc ctt cca ggt gcg ttc aac gtt<br>Asn Gln Ser Tyr Gln Val Glu Leu Ala Leu Pro Gly Ala Phe Asn Val<br>                    925                    930                    935 | 3854 |
| gct aac gcc acg ttg gca ttt gcc gct gcg gca ccg tgg gtg ttg atg<br>Ala Asn Ala Thr Leu Ala Phe Ala Ala Ala Ala Pro Trp Val Leu Met<br>940                      945                    950 | 3902 |
| gcg acg ttt gct cga ggc atg tcc aag gtc gcg gtt cca ggc cgt atg<br>Ala Thr Phe Ala Arg Gly Met Ser Lys Val Ala Val Pro Gly Arg Met<br>955                      960                    965 | 3950 |
| gaa cgc att gat gag gga caa gac ttc ctt gca gtg gtg gat tat gcc<br>Glu Arg Ile Asp Glu Gly Gln Asp Phe Leu Ala Val Val Asp Tyr Ala<br>970                      975                    980 | 3998 |

-continued

```
cac aag cct gct gca gtg gct gct gtg ttg gat acg ttg agg acc cag      4046
His Lys Pro Ala Ala Val Ala Ala Val Leu Asp Thr Leu Arg Thr Gln
985             990                 995                 1000 att gac ggg cgc ctc gga agt ggt tat cgg tgc tgg tgg aga cgc          4091
Ile Asp Gly Arg Leu Gly Ser Gly Tyr Arg Cys Trp Trp Arg Arg
            1005                1010                1015 gat tcc acc aag cgt ggc ccc atg ggc agt tgt ccg cac agg tct          4136
Asp Ser Thr Lys Arg Gly Pro Met Gly Ser Cys Pro His Arg Ser
        1020                1025                1030 gga tct agt tat tgt act gat gca aac ctc gtc aga gtg gct ggc          4181
Gly Ser Ser Tyr Cys Thr Asp Ala Asn Leu Val Arg Val Ala Gly
    1035                1040                1045 acg att cgc gca gca gtc act gca gga gca cag cag ggt gct tca          4226
Thr Ile Arg Ala Ala Val Thr Ala Gly Ala Gln Gln Gly Ala Ser
1050                1055                1060 gag tcc gaa cga ccg gtg gaa gtc cta gaa att ggt gac cgt gca          4271
Glu Ser Glu Arg Pro Val Glu Val Leu Glu Ile Gly Asp Arg Ala
                1065                1070                1075 gaa gca att cgc gtt ttg gtc gag tgg gca cag cct gga gat ggc          4316
Glu Ala Ile Arg Val Leu Val Glu Trp Ala Gln Pro Gly Asp Gly
            1080                1085                1090 att gta gta gct gga aaa ggc cat gaa gtt gga caa cta gtt gct          4361
Ile Val Val Ala Gly Lys Gly His Glu Val Gly Gln Leu Val Ala
        1095                1100                1105 ggt gtc acc cac cat ttt gat gac cgc gaa gaa ggt cgc gct gct          4406
Gly Val Thr His His Phe Asp Asp Arg Glu Glu Gly Arg Ala Ala
    1110                1115                1120 ttg aca gaa aag ctc aac aat aaa ctt ccc ctt act acg gaa gaa          4451
Leu Thr Glu Lys Leu Asn Asn Lys Leu Pro Leu Thr Thr Glu Glu
1125                1130                1135 gga taggccacag tc atg atc aca atg  acc ctt ggg gaa atc  gct gac      4499
Gly            Met Ile Thr Met  Thr Leu Gly Glu Ile  Ala Asp
                       1140                1145 atc gtt gga ggc agg cta act ggc ggt gct caa gaa gat acg ctt          4544
Ile Val Gly Gly Arg Leu Thr Gly Gly Ala Gln Glu Asp Thr Leu
        1150                1155                1160 gtg agc tcc agc gtg gaa ttt gat tct cga tcc ctc aca ccg ggt          4589
Val Ser Ser Ser Val Glu Phe Asp Ser Arg Ser Leu Thr Pro Gly
    1165                1170                1175 ggc ttg ttt tta gca ctt ccg ggt gct cgt gta gac ggc cat gat          4634
Gly Leu Phe Leu Ala Leu Pro Gly Ala Arg Val Asp Gly His Asp
1180                1185                1190 ttt gct gca act gca att gag aaa ggt gcg gtc gca gta ttg gca          4679
Phe Ala Ala Thr Ala Ile Glu Lys Gly Ala Val Ala Val Leu Ala
                1195                1200                1205 gcc cgt gag gtt gac gta cct gcg atc gtc gtg cct cca gta aaa          4724
Ala Arg Glu Val Asp Val Pro Ala Ile Val Val Pro Pro Val Lys
            1210                1215                1220 atc cag gaa tcc aat gct gac att tat gct cat gaa cca gat ggg          4769
Ile Gln Glu Ser Asn Ala Asp Ile Tyr Ala His Glu Pro Asp Gly
        1225                1230                1235 cat ggc gcg gcg gta gtg gag gcg ttg tct cgg ttg gct cgc cac          4814
His Gly Ala Ala Val Val Glu Ala Leu Ser Arg Leu Ala Arg His
    1240                1245                1250 gtg gtg gat atc tgc gtg gct ggc cat caa ttg aac gtt gtg gct          4859
Val Val Asp Ile Cys Val Ala Gly His Gln Leu Asn Val Val Ala
1255                1260                1265 att act ggt tct gcg gga aag act tct acg aag gat ttc atc gcg          4904
Ile Thr Gly Ser Ala Gly Lys Thr Ser Thr Lys Asp Phe Ile Ala
                1270                1275                1280
```

-continued

```
acg gtt ctt ggc caa gat ggg cca act gtg gca cct ccg ggc tcg       4949
Thr Val Leu Gly Gln Asp Gly Pro Thr Val Ala Pro Pro Gly Ser
        1285                1290                1295 ttt aac aat gag ctt ggt ttg cca cac acc gtc cgc tgc aca acc       4994
Phe Asn Asn Glu Leu Gly Leu Pro His Thr Val Arg Cys Thr Thr
            1300                1305                1310 gat act aag tat ttg gtg gct gag atg tcc gcg cgt ggc att gga       5039
Asp Thr Lys Tyr Leu Val Ala Glu Met Ser Ala Arg Gly Ile Gly
        1315                1320                1325 cat att aag cac ctg aca gag att cgt ccg cca cgg att gca gct       5084
His Ile Lys His Leu Thr Glu Ile Arg Pro Pro Arg Ile Ala Ala
        1330                1335                1340 gtg ctc aac gtc ggc cat gcg cac ctg ggt gaa ttt gga tcc cgc       5129
Val Leu Asn Val Gly His Ala His Leu Gly Glu Phe Gly Ser Arg
        1345                1350                1355 gag aat atc gcg cag gca aaa ggc gag atc att gaa gcg ctg ccc       5174
Glu Asn Ile Ala Gln Ala Lys Gly Glu Ile Ile Glu Ala Leu Pro
        1360                1365                1370 tcg aag aaa acg ggt ggg gta gca gtc ctt aac gct gac gat cct       5219
Ser Lys Lys Thr Gly Gly Val Ala Val Leu Asn Ala Asp Asp Pro
        1375                1380                1385 ttt gtc gcc cgg atg gct cca cgc act aag gcg cgc gtg gtg tgg       5264
Phe Val Ala Arg Met Ala Pro Arg Thr Lys Ala Arg Val Val Trp
        1390                1395                1400 ttt acc acc gat gca ggc caa gca aaa aag tct gat tat tgg gca       5309
Phe Thr Thr Asp Ala Gly Gln Ala Lys Lys Ser Asp Tyr Trp Ala
        1405                1410                1415 acg agt att tca ctg gac gct gtt gcg cgg gca agc                   5345
Thr Ser Ile Ser Leu Asp Ala Val Ala Arg Ala Ser
        1420                1425

<210> SEQ ID NO 2
<211> LENGTH: 581
<212> TYPE: PRT
<213> ORGANISM: Brevibacterium lactofermentum

<400> SEQUENCE: 2

Met Val Thr Arg Ile Ala Leu Val Ile Ala Gly Val Leu Ile Ile Arg
1               5                   10                  15

Leu Gly Trp Val Gln Val Val Trp Gly Pro Glu Leu Ser Leu Asn Ala
            20                  25                  30

Ser Glu Gln Arg Thr Arg Val Tyr Val Asp Pro Ala Arg Arg Gly Thr
        35                  40                  45

Ile Val Asp Arg Glu Gly Asn Gln Met Ala Tyr Thr Met Gln Ala Arg
    50                  55                  60

Ser Leu Thr Val Ser Pro Asn Ile Met Arg Glu Leu Lys Thr Gly
65                  70                  75                  80

Thr Asp Leu Ala Leu Arg Leu Ala Ala Glu Thr Asp Pro Glu Asn
            85                  90                  95

Val Ala Ser Tyr Val Thr Ile Glu Glu Gly Asn Ala Tyr Val Phe Ala
            100                 105                 110

Ser Glu Glu Gln Arg Glu Thr Ile Leu Ser Asp Lys Val Glu Glu Arg
        115                 120                 125

Ile Gln Ser Ile Ala Asp Arg Ile Pro Glu Ile Ile Lys Ser His Asp
    130                 135                 140

Gln Asp Val Thr Gly Ile Ser Ser Glu Glu Ile Leu Asp Lys Leu Asn
145                 150                 155                 160
```

```
Ala Asp Ser Gln Tyr Glu Val Leu Val Arg Asn Val Asp Pro Asp Val
            165                 170                 175

Ala Ser Glu Ile Thr Asp Glu Met Pro Ser Val Ala Ala Asp His Gln
            180                 185                 190

Asp Ile Arg Gln Tyr Pro Asn Gly Ala Ile Gly Glu Asn Ile Ile Gly
            195                 200                 205

Arg Ile Ser Met Asp Gly Glu Gly Gln Phe Gly Phe Glu Ala Ser Asn
            210                 215                 220

Asp Ser Leu Leu Ala Gly Asn Asn Gly Arg Ser Thr Gln Asp Met Ser
225                 230                 235                 240

Ile Leu Gly Gln Ala Ile Pro Gly Thr Leu Arg Asp Gln Ile Pro Ala
                245                 250                 255

Ile Asp Gly Ala Ser Val Glu Leu Thr Val Asp Leu Asp Leu Gln Thr
                260                 265                 270

Tyr Val Gln Gln Ala Leu Glu Gln Ala Lys Ala Asn Ser Gly Ala Glu
            275                 280                 285

Asn Ala Ser Ala Val Val Leu Asp Ala Glu Thr Ala Glu Val Leu Ala
            290                 295                 300

Met Ala Asn Thr Asp Thr Ile Asn Pro Asn Glu Asp Thr Gly Lys Gln
305                 310                 315                 320

Ile Glu Gln Gly Lys Ser Phe Asp Asn Pro Ser Val Thr His Pro Phe
                325                 330                 335

Glu Pro Gly Ser Val Ala Lys Val Ile Thr Ala Ala Gly Val Ile Gln
                340                 345                 350

Asp Gly Leu Thr Thr Pro Asp Glu Val Leu Gln Val Pro Gly Ser Ile
            355                 360                 365

Glu Met Ala Gly Val Ser Val Gly Asp Ala Trp Asp His Gly Val Val
            370                 375                 380

Pro Tyr Thr Thr Ala Gly Ile Phe Gly Lys Ser Ser Asn Val Gly Thr
385                 390                 395                 400

Leu Met Leu Ala His Gly Leu Gly Glu Asp Lys Phe Ala Asp Tyr Leu
                405                 410                 415

Glu Arg Phe Gly Val Gly Gln Ser Thr Gly Ile Glu Leu Pro Ser Glu
            420                 425                 430

Ser Gln Gly Leu Leu Pro Ala Arg Glu Gln Trp Ser Gly Gly Thr Phe
            435                 440                 445

Ala Asn Leu Pro Ile Gly Gln Gly Met Ser Ile Thr Thr Leu Gln Met
450                 455                 460

Ala Gly Ile Tyr Gln Ala Leu Ala Asn Asp Gly Glu Arg Ile Glu Pro
465                 470                 475                 480

Arg Ile Ile Lys Ser Val Thr Asp Ser Asp Gly Thr Val Leu Glu Gln
                485                 490                 495

Pro Glu Pro Asp Lys Ile Gln Val Val Ser Ala Glu Ala Ala Arg Thr
            500                 505                 510

Thr Val Asp Met Phe Arg Ser Val Thr Gln Val Asp Pro Leu Gly Val
            515                 520                 525

His Lys Val Pro Leu Gln Thr Pro Pro Leu Arg Val Ile Lys Ser Gln
            530                 535                 540

Val Arg Gln Val Arg Arg Lys Lys Leu Thr Pro Thr Arg Ala Arg Thr
545                 550                 555                 560
```

```
Leu Thr Arg Asn Thr Gly Leu Pro Ser Arg Val Leu His Pro Leu Met
                565                 570                 575

Ile Leu Asp Leu Leu
            580

<210> SEQ ID NO 3
<211> LENGTH: 555
<212> TYPE: PRT
<213> ORGANISM: Brevibacterium lactofermentum

<400> SEQUENCE: 3

Val Ser Phe Val Glu Phe His Asn Leu Asn Phe Cys Leu Asn Ser Phe
1               5                   10                  15

Arg His His Pro Arg Ala Ala Ser Glu Leu Leu Thr Pro Arg Asn Leu
            20                  25                  30

Trp Arg Glu Asn His Gly Asn His Val Ala Gly Pro His Gln Thr
        35                  40                  45

Tyr Arg Trp His Pro Gln Gly Leu Cys Gln Gly Val Pro Ala His Ala
    50                  55                  60

Val Gly Glu Gln Ala Ile Ala Ala Ile Gly Leu Asp Ser Ser Ser Leu
65                  70                  75                  80

Pro Thr Ser Asp Ala Ile Phe Ala Ala Val Pro Gly Thr Arg Thr His
                85                  90                  95

Gly Ala Gln Phe Ala Gly Thr Asp Asn Ala Ala Lys Ala Val Ala Ile
            100                 105                 110

Leu Thr Asp Ala Ala Gly Leu Glu Val Leu Asn Glu Ala Gly Glu Thr
        115                 120                 125

Arg Pro Ile Ile Val Val Asp Asp Val Arg Ala Val Leu Gly Ala Ala
    130                 135                 140

Ser Ser Ser Ile Tyr Gly Asp Pro Ser Lys Asp Phe Thr Leu Ile Gly
145                 150                 155                 160

Val Thr Gly Thr Ser Gly Lys Thr Thr Thr Ser Tyr Leu Leu Glu Lys
                165                 170                 175

Gly Leu Met Glu Ala Gly His Lys Val Gly Leu Ile Gly Thr Thr Gly
            180                 185                 190

Thr Arg Ile Asp Gly Glu Glu Val Pro Thr Lys Leu Thr Thr Pro Glu
        195                 200                 205

Ala Pro Thr Leu Gln Ala Leu Phe Ala Arg Met Arg Asp His Gly Val
    210                 215                 220

Thr His Val Val Met Glu Val Ser Ser His Ala Leu Ser Leu Gly Arg
225                 230                 235                 240

Val Ala Gly Ser His Phe Asp Val Ala Ala Phe Thr Asn Leu Ser Gln
                245                 250                 255

Asp His Leu Asp Phe His Pro Thr Met Asp Asp Tyr Phe Asp Ala Lys
            260                 265                 270

Ala Leu Phe Phe Arg Ala Asp Ser Pro Leu Val Ala Asp Lys Gln Val
        275                 280                 285

Val Cys Val Asp Asp Ser Trp Gly Gln Arg Met Ala Ser Val Ala Ala
    290                 295                 300

Asp Val Gln Thr Val Ser Thr Leu Gly Gln Glu Ala Asp Phe Ser Ala
305                 310                 315                 320

Thr Asp Ile Asn Val Ser Asp Ser Gly Ala Gln Ser Phe Lys Ile Asn
                325                 330                 335

Ala Pro Ser Asn Gln Ser Tyr Gln Val Glu Leu Ala Leu Pro Gly Ala
            340                 345                 350
```

-continued

```
Phe Asn Val Ala Asn Ala Thr Leu Ala Phe Ala Ala Ala Pro Trp
        355                 360                 365
Val Leu Met Ala Thr Phe Ala Arg Gly Met Ser Lys Val Ala Val Pro
    370                 375                 380
Gly Arg Met Glu Arg Ile Asp Glu Gly Gln Asp Phe Leu Ala Val Val
385                 390                 395                 400
Asp Tyr Ala His Lys Pro Ala Val Ala Ala Val Leu Asp Thr Leu
                405                 410                 415
Arg Thr Gln Ile Asp Gly Arg Leu Gly Ser Gly Tyr Arg Cys Trp Trp
            420                 425                 430
Arg Arg Asp Ser Thr Lys Arg Pro Met Gly Ser Cys Pro His Arg
        435                 440                 445
Ser Gly Ser Ser Tyr Cys Thr Asp Ala Asn Leu Val Arg Val Ala Gly
    450                 455                 460
Thr Ile Arg Ala Ala Val Thr Ala Gly Ala Gln Gln Gly Ala Ser Glu
465                 470                 475                 480
Ser Glu Arg Pro Val Glu Val Leu Glu Ile Gly Asp Arg Ala Glu Ala
                485                 490                 495
Ile Arg Val Leu Val Glu Trp Ala Gln Pro Gly Asp Gly Ile Val Val
            500                 505                 510
Ala Gly Lys Gly His Glu Val Gly Gln Leu Val Ala Gly Val Thr His
        515                 520                 525
His Phe Asp Asp Arg Glu Glu Gly Arg Ala Ala Leu Thr Glu Lys Leu
    530                 535                 540
Asn Asn Lys Leu Pro Leu Thr Thr Glu Glu Gly
545                 550                 555

<210> SEQ ID NO 4
<211> LENGTH: 293
<212> TYPE: PRT
<213> ORGANISM: Brevibacterium lactofermentum

<400> SEQUENCE: 4

Met Ile Thr Met Thr Leu Gly Glu Ile Ala Asp Ile Val Gly Gly Arg
1               5                   10                  15
Leu Thr Gly Gly Ala Gln Glu Asp Thr Leu Val Ser Ser Val Glu
        20                  25                  30
Phe Asp Ser Arg Ser Leu Thr Pro Gly Gly Leu Phe Leu Ala Leu Pro
    35                  40                  45
Gly Ala Arg Val Asp Gly His Asp Phe Ala Ala Thr Ala Ile Glu Lys
50                  55                  60
Gly Ala Val Ala Val Leu Ala Ala Arg Glu Val Asp Val Pro Ala Ile
65                  70                  75                  80
Val Val Pro Pro Val Lys Ile Gln Glu Ser Asn Ala Asp Ile Tyr Ala
                85                  90                  95
His Glu Pro Asp Gly His Gly Ala Ala Val Val Glu Ala Leu Ser Arg
            100                 105                 110
Leu Ala Arg His Val Val Asp Ile Cys Val Ala Gly His Gln Leu Asn
        115                 120                 125
Val Val Ala Ile Thr Gly Ser Ala Gly Lys Thr Ser Thr Lys Asp Phe
    130                 135                 140
Ile Ala Thr Val Leu Gly Gln Asp Gly Pro Thr Val Ala Pro Pro Gly
145                 150                 155                 160
Ser Phe Asn Asn Glu Leu Gly Leu Pro His Thr Val Arg Cys Thr Thr
                165                 170                 175
```

```
Asp Thr Lys Tyr Leu Val Ala Glu Met Ser Ala Arg Gly Ile Gly His
            180                 185                 190

Ile Lys His Leu Thr Glu Ile Arg Pro Pro Arg Ile Ala Ala Val Leu
        195                 200                 205

Asn Val Gly His Ala His Leu Gly Glu Phe Gly Ser Arg Glu Asn Ile
    210                 215                 220

Ala Gln Ala Lys Gly Glu Ile Ile Glu Ala Leu Pro Ser Lys Lys Thr
225                 230                 235                 240

Gly Gly Val Ala Val Leu Asn Ala Asp Asp Pro Phe Val Ala Arg Met
                245                 250                 255

Ala Pro Arg Thr Lys Ala Arg Val Val Trp Phe Thr Thr Asp Ala Gly
                260                 265                 270

Gln Ala Lys Lys Ser Asp Tyr Trp Ala Thr Ser Ile Ser Leu Asp Ala
            275                 280                 285

Val Ala Arg Ala Ser
    290

<210> SEQ ID NO 5
<211> LENGTH: 30
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 5
gcgcgaattc cgcaacctcg tcgtgacatg                                    30

<210> SEQ ID NO 6
<211> LENGTH: 34
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 6
gcgcgaattc aagaccaata gccgcgattg cttg                               34
```

PENICILLIN BINDING PROTEIN GENE AND PROCESS FOR PRODUCING L-GLUTAMIC ACID

TECHNICAL FIELD

The present invention relates to a method for producing L-glutamic acid by fermentation. L-glutamic acid is widely used as a raw material of seasonings and so forth.

BACKGROUND ART

If coryneform bacteria are cultured in a medium containing a restricted amount of biotin, the bacteria produce a marked amount of L-glutamic acid. On the other hand, if coryneform bacteria are cultured in a medium containing an excessive amount of biotin, the bacteria do not produce L-glutamic acid. However, it is known that, even under such a condition, if a surface active agent or a biotin activity suppressor such as penicillin is added to the medium, growth of the bacteria is suppressed and they become to produce a marked amount of L-glutamic acid.

The glutamic acid production induced by addition of penicillin to a medium has been studied for many years (T. D. Nunheimer, J. Birnbaum, E. D. Ihnen and A. L. Demasin, *Appl. Microbiol.*, 20, 215–217 (1970)). The effect of penicillin is considered to cause structural change of cellular surface layers, thereby enhancing permeability of cytoplasmic membranes for glutamic acid.

In addition, it has also been studied through what kind of mechanism the restriction of the biotin amount or the addition of a surface active agent or penicillin influences the productivity of L-glutamic acid of coryneform bacteria, and presence of a gene considered to participate in the L-glutamic acid production has been elucidated (dtsR gene). Further, it has been confirmed that a strain of which dtsR gene is disrupted produces a marked amount of L-glutamic acid even under a condition in which biotin is present in such an amount that a wild strain hardly produces L-glutamic acid (International Patent Publication WO95/23224).

Furthermore, there have been obtained many findings that contradicts the explanation that the glutamic acid production is induced the enhancement of permeability of cytoplasmic membranes, and the mechanism of the glutamic acid production induced by penicillin has still been unknown (E. Kimura, Y. Kawahara and W. Nakamatsu, *Tanpakusshitu Kakusan Koso* (*Protein, Nucleic acid and Enzyme*), vol. 42, pp. 2633–2640 (1997)).

By the way, it is well known that penicillin binding proteins (PBPs) play an important role in bacterial cell division. The penicillin binding proteins are considered to be enzymes that exist in bacterial cellular surface layers, and they specifically bind to β-lactam antibiotics such as penicillin. Although it may vary depending on the species, it is considered that 3–8 kinds of the proteins are usually found in *Escherichia coli*, and their molecular weights are distributed around the range of 40,000–120,000. Penicillin inhibits the enzymatic reactions by binding to a serine residue of an active site of the penicillin binding proteins.

It has been elucidated that 7 kinds of penicillin binding proteins exist in *Escherichia coli* (*E. coli*), which was especially a main target of researches (B. G. Spratt, *Proc. Natl. Acad. Sci. U.S.A.*, 72, 2999 (1975)). Among those, those designated as PBP2 and PBP3 have been demonstrated to play an important role in cell division (B. G. Spratt, *J. Bacteriol.*, 131, 293 (1977)). However, it has not been known whether penicillin binding proteins exists in coryneform bacteria.

DISCLOSURE OF THE INVENTION

The inventors of the present invention investigated whether penicillin binding proteins (abbreviates as "PBPs" hereinafter) should exist also in coryneform bacteria, and analyzed their functions. As a result, the inventors obtained a novel finding considered to be useful for elucidating the mechanism of the glutamic acid production in coryneform bacteria induced by penicillin, and at the same time, they found that the finding could be utilized for developments concerning the improvement of glutamic acid producing ability of coryneform bacteria from a viewpoint that had not been known yet.

The present invention was accomplished on the basis of the aforementioned findings, and it relates to a method for producing L-glutamic acid, comprising the steps of cultivating a coryneform bacterium in a liquid medium to produce and accumulate L-glutamic acid in the medium, and collecting the L-glutamic acid, wherein PBP does not normally function in the bacterium and the bacterium has the ability to produce L-glutamic acid In a preferred embodiment of the present invention, the coryneform bacterium used in the aforementioned method is a bacterium in which PBP functions normally at the first temperature and does not function normally at the second temperature, and the method comprises a step of cultivating the bacterium at the first temperature to proliferate the bacterium and a step of cultivating the bacterium at the second temperature to produce L-glutamic acid.

In another embodiment of the present invention, the coryneform bacterium used in the aforementioned method is a bacterium which harbors a plasmid containing a gene coding for PBP (PBP gene) and a temperature sensitive replication control region, and in which the PBP gene on chromosome does not function, and the plasmid can replicate at the first temperature, and cannot replicate at the second temperature.

In a further embodiment of the present invention, PBP produced by the coryneform bacterium used in the method has a temperature sensitive mutation.

In a still further embodiment of the present invention, PBP shows a molecular weight of about 60,000 in SDS-polyacrylamide gel electrophoresis, when PBP binds to penicillin G.

The second aspect of the present invention is DNA which codes for a protein defined in the following (A) or (B):

(A) a protein which has the amino acid sequence of SEQ ID NO: 2 in Sequence Listing;

(B) a protein which has an amino acid sequence of SEQ ID NO: 2 in Sequence Listing including substitution, deletion, insertion, addition or inversion of one or several amino acids, and an activity for binding to penicillin.

In a preferred embodiment of the invention, the aforementioned DNA is DNA defined in the following (a) or (b):

(a) DNA which comprises at least the nucleotide sequence of the nucleotide numbers 881 to 2623 of SEQ ID NO: 1 in Sequence Listing;

(b) DNA which is hybridizable with a nucleotide sequence comprising at least the sequence of the nucleotide numbers 881 to 2623 of SEQ ID NO: 1 in Sequence Listing under a stringent condition, and codes for a protein having an activity for binding to penicillin.

Hereafter, the present invention will be explained in detail.

<1> PBP of Coryneform Bacteria

In the present invention, coryneform bacteria include those bacteria having been hitherto classified into the genus *Brevibacterium* but united into the genus *Corynebacterium* at present (*Int. J. Syst. Bacteriol.*, 41, 255 (1981)), and include bacteria belonging to the genus *Brevibacterium* closely relative to the genus *Corynebacterium*. Examples of such coryneform bacteria are listed below.

*Corynebacterium acetoacidophilum*
*Corynebacterium acetoglutamicum*
*Corynebacterium callunae*
*Corynebacterium glutamicum*
*Corynebacterium lilium* (*Corynebacterium glutamicum*)
*Corynebacterium melassecola*
*Brevibacterium divaricatum*
(*Corynebacterium glutamicum*)
*Brevibacterium flavum* (*Corynebacterium glutamicum*)
*Brevibacterium immariophilum*
*Brevibacterium lactofermentum*
(*Corynebacterium glutamicum*)
*Brevibacterium roseum*
*Brevibacterium saccharolyticum*
*Brevibacterium thiogenitalis*
*Corynebacterium thermoaminogenes*

Specifically, the following strains can be exemplified.

*Corynebacterium acetoacidophilum* ATCC 13870
*Corynebacterium acetoglutamicum* ATCC 15806
*Corynebacterium callunae* ATCC 15991
*Corynebacterium glutamicum* ATCC 13020
*Corynebacterium lilium* (*Corynebacterium glutamicum*) ATCC 15990
*Corynebacterium melassecola* ATCC 17965
*Brevibacterium divaricatum*
(*Corynebacterium glutamicum*) ATCC 14020
*Brevibacterium flavum* (*Corynebacterium glutamicum*) ATCC 14067
*Brevibacterium immariophilum* ATCC 14068
*Brevibacterium lactofermentum*
(*Corynebacterium glutamicum*) ATCC 13869
*Brevibacterium roseum* ATCC 13825
*Brevibacterium saccharolyticum* ATCC 14066
*Brevibacterium thiogenitalis* ATCC 19240
*Corynebacterium thermoaminogenes* AJ12340
(FERM BP-1539)

PBP referred to in the present invention is a membrane protein that exists in the cellular surface layers of the above coryneform bacteria, and if it contacts with penicillin, it binds thereto with a covalent bond. PBP can be detected by, for example, adding labeled penicillin to a membrane fraction of coryneform bacteria to allow a reaction, subjecting a surface active agent-soluble fraction to electrophoresis on polyacrylamide gel, and visualizing the label (penicillin binding test). As shown in the examples mentioned below, PBPs of *Brevibacterium lactofermentum* are detected as three bands at molecular weights of about 110 kDa, 100 kDa and 60 kDa in SDS polyacrylamide gel electrophoresis (SDS-PAGE) in a state that they bind to penicillin G, and they were designated as PBP1, PBP2 and PBP3.

When affinity between these PBPs and mecillinam, which is a derivative of penicillin G, was investigated, it was found that mecillinam selectively binds to PBP3. Further, it was found that, when *Brevibacterium lactofermentum* was cultured under a condition that biotin was present in a significant amount, L-glutamic acid was produced in the presence of a certain concentration of mecillinam. These facts suggested that L-glutamic acid production could be induced in the presence of a significant amount of biotin by inhibiting the function of PBPs, at least PBP3. Therefore, a coryneform bacterium in which PBP does not normally function should come to be able to induce L-glutamic acid production without addition of a biotin activity suppressor even in the presence of a significant amount of biotin. Moreover, there is possibility that such a coryneform bacterium in which PBP does not normally function should have improved L-glutamic acid producing ability. Furthermore, a novel finding concerning the L-glutamic acid production of coryneform bacteria should be obtained by manipulating a PBP gene, and it can be utilized for development from an aspect that have not been known yet.

In the present invention, the expression "PBP does not normally function" means a state that the L-glutamic acid production is induced in the presence of a significant amount of biotin. It may be a state that PBP is not produced because of inhibition of transcription or translation of a PBP gene, or a state that the function of PBP is reduced or eliminated because of a mutation occurring in the produced PBP.

<2> Coryneform Bacterium in Which PBP Does not Function Normally

The coryneform bacterium used for the method for producing of L-glutamic acid according to the present invention is a coryneform bacterium in which PBP does not function normally. In a preferred embodiment, the coryneform bacterium used in the aforementioned method is a bacterium in which PBP functions normally under the first culture condition and does not function normally under the second culture condition. Such a coryneform bacterium can proliferate under the first culture condition, and can produce L-glutamic acid under the second culture condition in the presence of a significant amount of biotin. As PBP, PBP3 is preferred.

As the aforementioned culture condition, there can be mentioned temperature of culture, osmotic pressure of medium, pH, components of medium and so forth. Examples of the components of medium include an inducer such as IPTG (isopropyl-β-D-thiogalactopranoside) and acetic acid, and a suppressor such as glucose. The culture temperature will be explained as an example of the culture condition in the description hereinafter. However, concerning other culture conditions, the term "temperature" in the following description can be replaced with a term indicating another condition.

As an example of the coryneform bacterium in which PBP does not function normally, there can be mentioned a mutant strain in which a mutation is introduced into a gene coding for PBP (PBP gene) so that PBP that functions normally should not be expressed. The aforementioned mutation may be a mutation that inhibits transcription or translation of the PBP gene, or a mutation that produces PBP that does not function normally.

Since a mutation that causes complete deficiency of PBP should be fatal to the bacteria, the aforementioned mutant strain can be obtained as a conditional mutant strain such as a temperature sensitive mutant strain. Such a mutant strain can be obtained by, for example, treating a coryneform bacterium by ultraviolet irradiation or with a chemical agent to obtain mutant strains that can proliferate at the first temperature (for example, low temperature) but cannot proliferate at the second temperature (for example, high temperature), and selecting, from the obtained mutant strains, a mutant strain that can proliferate at the first temperature and produces L-glutamic acid in the presence of a significant amount of biotin when it is cultured at the second temperature. As a mutant strain that represents such a characteristic, a DTSR protein deficient strain (International Patent Publication WO95/23224) or an α-KGDH deficient strain (International Patent Publication WO95/34672) may be selected. However, it can be confirmed if a candidate strain is a mutant strain having a mutation concerning PBP by performing the aforementioned penicillin binding test for the cells cultured at the second temperature.

If such a mutant strain is once obtained, a PBP gene of the coryneform bacterium can be cloned by using the mutant strain as a host. That is, a DNA fragment containing a PBP gene can be obtained by transforming the mutant strain in which PBP does not function normally with a plasmid containing chromosomal DNA derived from coryneform bacteria, selecting a transformant strain in which PBP functions normally, and collecting the plasmid.

Techniques used for usual gene recombination such as those for digestion and ligation of DNA, transformation, extraction of recombinant DNA from transformants, colony hybridization and so forth are described in references well known to those skilled in the art, for example, J. Sambrook, E. F. Fritsch, and T. Maniatis, Molecular Cloning, Cold Spring Harbor Laboratory Press (1989) and so forth.

A chromosomal DNA library can be produced, for example, as follows. First, chromosomal DNA is prepared by the method of Miura et al. (H. Saito, and K. Miura, Biochem. Biophys. Acta, 72, 619 (1963)) or the like. Then, the chromosomal DNA is partially digested with a suitable restriction enzyme to obtain a mixture of various fragments. If the degree of the digestion is controlled by adjusting digestion reaction time or the like, restriction enzymes of a wide range can be used. For example, the chromosomal DNA is digested by allowing Sau3AI to act on it at a temperature of 30° C. or higher, preferably 37° C. or higher, for various periods of time (1 minute to 2 hours) at an enzyme concentration of 1–10 units/ml.

Subsequently, the digested chromosomal DNA fragments are ligated to vector DNA autonomously replicable within *Escherichia coli* cells to produce recombinant DNA. More specifically, a restriction enzyme producing the same end nucleotide sequence as the restriction enzyme used for the digestion of the chromosomal DNA, Sau3AI, for example, BamHI, is allowed to act on the vector DNA at a temperature of 30° C. or higher for 1 hour or more, preferably 1–3 hours, at an enzyme concentration of 1–100 units/ml to fully digest the vector and cleave it. Then, the mixture of the chromosomal DNA fragments and the cleaved vector DNA obtained as described above are mixed, and a DNA ligase, preferably T4 DNA ligase, is allowed to act on the mixture at a temperature of 4–16° C. for 1 hour or more, preferably 6–24 hours, at an enzyme concentration of 1–100 units/ml to obtain recombinant DNA.

The vector autonomously replicable in *Escherichia coli* cells is preferably a plasmid vector autonomously replicable in the host cell, and examples thereof include pUC19, pUC18, pBR322, pHSG299, pHSG399, pHSG398, RSF1010 and so forth.

Moreover, if a DNA fragment having an ability to make a plasmid autonomously replicable in coryneform bacteria (it can be prepared from, for example, pAM330 (refer to Japanese Patent Laid-open (Kokai) No. 58-67699), pHM1519 (refer to Japanese Patent Laid-open No. 58-77895), pCG1 (refer to Japanese Patent Laid-open No. 57-134500), pCG2 (refer to Japanese Patent Laid-open No. 58-35197), pCG4 (refer to Japanese Patent Laid-open No. 57-183799), pCG11 (refer to Japanese Patent Laid-open No. 57-183799) and so forth) is inserted into the aforementioned vectors, they can be used as a so-called shuttle vector autonomously replicable in both of *Escherichia coli* and coryneform bacteria.

Examples of such a shuttle vector include those mentioned below. There are also indicated microorganisms that harbor each vector, and accession numbers thereof at international depositories are shown in the parentheses, respectively.

| | |
|---|---|
| pAJ655: | *Escherichia coli* AJ11882 (FERM BP-136) |
| | *Corynebacterium glutamicum* SR8201 (ATCC 39135) |
| pAJ1844: | *Escherichia coli* AJ11883 (FERM BP-137) |
| | *Corynebacterium glutamicum* SR8202 (ATCC39136) |
| pAJ611: | *Escherichia coli* AJ11884 (FERM BP-138) |
| pAJ3148: | *Corynebacterium glutamicum* SR8203 (ATCC 39137) |
| pAJ440: | *Bacillus subtilis* AJ11901 (FERM BP140) |

By using the obtained recombinant DNA, for example, *Escherichia coli* K-12 strain is transformed to prepare a chromosomal DNA library. This transformation can be performed by the method of D. M. Morrison (*Methods in Enzymology*, 68, 326, 1979), the method comprising treatment of recipient cells with calcium chloride to increase their permeability for DNA (M. Mandel, and A. Higa, *J. Mol., Biol.,* 53, 159 (1970)) or the like.

Then, a mutant strain of a coryneform bacterium in which PBP does not function normally is transformed with the obtained chromosomal DNA library. As the method for transformation of coryneform bacteria, there is the aforementioned method utilizing a treatment of cells with calcium chloride or a method comprising allowing cells at a particular growth phase where they can take up DNA to take up it (reported for *Bacillus subtilis* by C. H. Duncan et al.). In addition to these, also employable is a method of making DNA-recipient cells into protoplasts or spheroplasts which can easily take up recombinant DNA, followed by allowing introduction of the recombinant DNA into the cells, which is known to be applicable to *Bacillus subtilis*, actinomycetes and yeasts (S. Chang, et al., *Molec. Gen. Genet.,* 168, 111 (1979); Bibb, et al., *Nature,* 274, 398 (1978); A. Hinnen, et al., *Proc. Natl. Sci. USA,* 75, 1929 (1978)). Other than those, a method for transformation of coryneform bacteria is also disclosed in Japanese Patent Laid-open No. 2-207791).

A transformant strain introduced with a PBP gene can be obtained by plating the transformed mutant strain under a condition where a mutant strain (host) that is not transformed cannot grow, and selecting a strain that has formed a colony. A DNA fragment containing a PBP gene can be obtained from the obtained transformant by isolating the recombinant DNA, for example, by the method of P. Guerry, et al. (*J. Bacteriol.,* 116, 1064 (1973)), the method of D. B. Clewell (*J. Bacteriol.,* 110, 667 (1972)) or the like. A coryneform bacterium transformed with recombinant DNA containing a PBP gene can also possibly be obtained by hybridization using a gene coding for a known PBP of a microorganism, for example, PBP of *Escherichia coli*, or an oligonucleotide produced based on the nucleotide sequence thereof.

Besides the mutagenesis treatment, a coryneform bacterium in which PBP does not function normally can be created by using a PBP gene obtained as described above. A PBP gene on chromosome can be disrupted by transforming a coryneform bacterium with DNA containing a PBP gene modified with internal deletion so as not to produce PBP functioning normally (deletion type PBP gene), and allowing recombination between the deletion type PBP gene and the PBP gene on the chromosome. Such gene destruction by homologous recombination has already been established, and there are methods utilizing a linear DNA, a plasmid that contains a temperature sensitive replication control region and so forth. In the present invention, the method utilizing a plasmid that contains a temperature sensitive replication control region is preferred.

A PBP gene on host chromosome can be replaced with the deletion type PBP gene as follows. That is, recombinant DNA is first prepared by inserting a temperature sensitive replication control region, mutant PBP gene and marker gene for resistance to a drug such as chloramphenicol, with which recombinant DNA a coryneform bacterium is transformed. Further, the resultant transformant strain is cultured at a temperature at which the temperature sensitive replication control region does not function, and then the transformant strain can be cultured in a medium containing the drug to obtain a transformant strain in which the recombinant DNA is incorporated into the chromosomal DNA.

In such a strain in which recombinant DNA is incorporated into chromosomal DNA, the mutant PBP gene is recombined with the PBP gene originally present on the chromosome, and the two fusion genes of the chromosomal PBP gene and the deletion type PBP gene are inserted into the chromosome so that the other portions of the recombinant DNA (vector segment, temperature sensitive replication control region and drug resistance marker) should be present between the two fusion genes. Therefore, the transformant expresses PBP, because the normal PBP gene is dominant in this state, and it can grow.

Then, in order to leave only the deletion type PBP gene on the chromosomal DNA, one copy of the PBP gene is eliminated together with the vector segment (including the temperature sensitive replication control region and the drug resistance marker) from the chromosomal DNA by recombination of the two PBP genes. In that case, the normal PBP gene is left on the chromosomal DNA, and the deletion type PBP gene is excised from the chromosomal DNA, or to the contrary, the deletion type PBP gene is left on the chromosomal DNA, and the normal PBP gene is excised from the chromosome DNA. In the both cases, the excised DNA may be retained in the cell as a plasmid when the cell is cultured at a temperature at which the temperature sensitive replication control region can function. Subsequently, the cell is cultured at a temperature at which the temperature sensitive replication control region cannot function. In the culture, the cell cannot proliferate when the deletion type PBP gene is left on the chromosomal DNA, since the plasmid containing the normal PBP gene is dropped from the cell. On the other hand, when the normal PBP gene is left on the chromosomal DNA, the cell can proliferate. Thus, a strain in which the PBP gene on the chromosomal DNA is disrupted and the normal PBP gene is harbored on the plasmid can be obtained by selecting a strain that can proliferate at a temperature at which the temperature sensitive replication control region functions, but cannot proliferate at a temperature at which the temperature sensitive replication control region does not function.

When the strain with the disrupted PBP gene obtained as described above is cultured at a temperature at which the temperature sensitive replication control region functions (for example, low temperature), it retains the PBP gene in the cell, and when it is cultured at a temperature at which the temperature sensitive replication control region does not function (for example, high temperature), it loses the PBP gene. In the following description, a temperature at which a temperature sensitive plasmid cannot replicate is referred to as a high temperature. However, it is not intended to exclude possibility that the temperature is a low temperature, and if a temperature sensitive replication control region is obtained which cannot replicate at a low temperature but can replicate at a high temperature, it may also be used.

A strain which is made recA⁻ after the PBP gene on chromosome DNA is disrupted and the normal PBP gene is incorporated into a plasmid is preferably used as the microorganism used in the present invention, since in such a strain, incorporation of the PBP gene on the plasmid into the chromosome during culture at a low temperature is prevented and thus the drop of the gene is secured.

The temperature sensitive replication control region can be obtained by subjecting a plasmid autonomously replicable in a coryneform bacterium cell and having drug resistance to a mutagenesis treatment, transforming a coryneform bacterium with the plasmid and extracting a plasmid from a transformant that can grow at a low temperature but cannot grow at a high temperature in a medium containing the drug.

As the method for the mutagenesis of plasmid, there can be mentioned the method utilizing an in vitro treatment of plasmid with hydroxylamine (G. O. Humpherys, et al., Molec. Gen. Genet., 145, 101–108 (1976) etc.).

The terms "low temperature" and "high temperature" herein used have relative concepts, and the border between the low temperature and the high temperature is not particularly limited. The "low temperature" means a temperature range wherein coryneform bacteria can at least proliferate when they are cultured. The "high temperature" means a temperature wherein coryneform bacteria themselves shall not die. The border of the low temperature and the high temperature can be determined by cultivating a transformant harboring a temperature sensitive plasmid in a medium containing a drug at various temperatures to determine a lower limit temperature above which the transformant cannot grow.

Examples of the plasmid that has a temperature sensitive replication control region functioning in a coryneform bacterium cell include pHS4, pHS22 and pHS23. Plasmid pHSC4, which is obtained by ligating a DNA fragment excised from pHS4 and containing a replication control region derived from a coryneform bacterium to a vector for *Escherichia coli*, pHSG398, can also be used for the present invention as a temperature sensitive plasmid. pHSC4 autonomously proliferates in coryneform bacteria and *Escherichia coli*, and it imparts chloramphenicol resistance to a host. *Escherichia coli* AJ12571 harboring pHSC4 was deposited at the National Institute of Bioscience and Human-Technology, the Agency of Industrial Science and Technology, the Ministry of International Trade and Industry on Oct. 11, 1990, and received an accession number of FERM P-11763. Then, it was transferred to an international deposit under the provisions of the Budapest Treaty on Aug. 26, 1991, and received an accession number of FERM BP-3524.

These temperature sensitive plasmids can autonomously proliferate at about 10–32° C. in a coryneform bacterium cell, but they cannot autonomously proliferate at about 34° C. or higher.

A DNA fragment that has a temperature sensitive replication control region can be obtained by, for example, digesting the aforementioned pHSC4 with BamHI and KpnI.

Construction of the aforementioned plasmids and nucleotide sequences of the regions containing a temperature sensitive replication control region thereof are disclosed in Japanese Patent Publication (Kokoku) No. 7-108228.

It is also known that, in *Escherichia coli*, some of a penicillin binding protein genes form a gene cluster, and murE gene and PBP3 gene (ftsI) are located closely to each other (F. Ishino, Nippon Nogeikagaku Kaishi, vol. 63, No. 11, 1755–1764 (1989)). Therefore, a PBP gene may be obtained together with the murE gene by transforming a murE temperature sensitive mutant as a host, which has been already obtained for coryneform bacteria, with a plasmid containing chromosomal DNA derived from a coryneform bacterium to obtain a transformant strain that has come to be able to grow at a temperature at which the host cannot grow. The inventors of the present invention successfully obtained a PBP gene based on this concept as described in the examples mentioned below.

Further, since the nucleotide sequences of the PBP gene and flanking regions were elucidated by the present invention, the PBP gene can readily be obtained by preparing primers based on the sequence and performing PCR (polymerase chain reaction; refer to T. J. White, et al., *Trends Genet.*, 5, 185 (1989)) utilizing coryneform bacterium chromosomal DNA as a template.

The nucleotide sequence containing the PBP gene obtained in the examples mentioned later is shown as SEQ ID NO: 1 in Sequence Listing. In this nucleotide sequence, there exist three opening reading frames (ORF) (nucleotide numbers 881–2623, 2790–4454 and 4467–5345). The amino acid sequences encoded by the ORFs are shown as SEQ ID NOS: 2–4.

When an existing protein database was searched for sequences exhibiting homology with these amino acid sequences, it was found that the amino acid sequence encoded by the first OFR showed homology of about 31% with the amino acid sequence encoded by the PBP3 gene (ftsI) of *Escherichia coli* on the amino acid level. The amino acid sequences encoded by the second and the third OFRs showed homology to the amino acid sequences encoded by the murE gene and the murF gene of *Escherichia coli*, respectively. These results suggested that the first OFR is the PBP gene corresponding to the ftsI of *Escherichia coli*.

The PBP gene of the present invention may code for substitution, deletion, insertion, addition or inversion of one or several amino acids, so long as the activity of the encoded protein for binding to penicillin is not degraded. The number meant by the term "several" used herein may vary depending on locations in the three-dimensional structure of proteins and kinds of amino acid residues. This is due to the fact that there are analogous amino acids among amino acids such as isoleucine and valine, and difference among such amino acids does not substantially affect the three-dimensional structure of proteins. Therefore, the encoded protein may be one having homology of 30–40% or more, preferably 55–65% or more, with respect to the entire amino acid sequence constituting the protein, and having the activity for binding to penicillin.

Such DNA encoding a protein substantially the same as a penicillin binding protein as mentioned above can be obtained by modifying the nucleotide sequence by, for example, the site-directed mutagenesis so that the amino acid residues of a specific site should include substitution, deletion, insertion, addition or inversion. Such modified DNA as mentioned above can also be obtained by an already known mutagenesis treatment. Examples of the mutagenesis treatment include in vitro treatment of DNA coding for a penicillin binding protein with hydroxylamine etc., treatment of a microorganism having DNA coding for a penicillin binding protein, for example, *Escherichia* bacteria, by ultraviolet irradiation or with a mutagenizing agent used for usual mutagenesis treatment such as N-methyl-N'-nitro-N-nitrosoguanidine (NTG) or nitrous acid.

The substitution, deletion, insertion, addition or inversion of nucleotides described above also includes mutation (mutant or variant) that naturally occurs due to individual difference, difference in species or genera of the microorganism having a penicillin binding protein.

DNA coding for substantially the same protein as a penicillin binding protein can be obtained by expressing DNA having such a mutation as described above in an appropriate cell, and examining the penicillin binding activity of an expressed product. DNA coding for substantially the same protein as a penicillin binding protein can also be obtained by isolating DNA hybridizable with DNA having, for example, the nucleotide sequence of nucleotide numbers 881 to 2623 in SEQ ID NO: 1 in Sequence Listing under a stringent condition and coding for a protein having the penicillin binding activity from DNA coding for penicillin binding protein having mutation or from a cell harboring it. The "stringent condition" referred to herein is a condition under which a so-called specific hybrid is formed, and a non-specific hybrid is not formed. It is difficult to clearly express this condition by using numerical values. However, for example, the stringent condition includes a condition under which two of DNA having high homology, for example, two of DNA having homology of not less than 50% are hybridized with each other, and two of DNA having homology lower than the above are not hybridized with each other. Alternatively, the stringent condition is exemplified by a condition under which two of DNA are hybridized with each other at a salt concentration corresponding to an ordinary condition of washing in Southern hybridization, i.e., 60° C., 1×SSC, 0.1% SDS, preferably 0.1×SSC, 0.1% SDS.

The genes hybridizable under the condition as described above includes those having a stop codon generated in the gene, and those having no activity due to mutation of the active center. However, such mutant genes can be easily removed by ligating the genes with a commercially available activity expression vector, and measuring the penicillin binding activity.

<3> Production of L-Glutamic Acid

L-Glutamic acid can be produced by cultivating such a coryneform bacterium as described above in which PBP does not function normally and which has L-glutamic acid producing ability in a liquid medium to produce and accumulate L-glutamic acid in the medium, and collecting the L-glutamic acid. According to the method of the present invention, L-glutamic acid can be produced in a medium containing a significant amount of biotin such as molasses without adding a biotin activity inhibitor.

When the coryneform bacterium used is a bacterium of which PBP normally functions at the first temperature and does not normally function at the second temperature, the bacterium is cultured at the first temperature to allow it to proliferate, and then cultured with shifting the temperature to the second temperature to produce L-glutamic acid.

Specifically, the temperature shifting can be attained by, for example, performing seed culture at a low temperature and performing culture in a main medium (main culture) at a high temperature. The temperature may also be shifted during preculture or main culture. The step of cell proliferation and the step of drop of plasmid are not clearly distinguished, and the step of drop of plasmid is accompanied with proliferation of cells.

As for the timing of the temperature shift, the period for the culture at a low temperature can readily be decided by carrying out preliminarily experiments with various periods of culture until the temperature shift. In general, the culture can be continued until a desired cell density is attained in the logarithmic growth phase, and then the temperature can be shifted to a level at which the plasmid cannot replicate.

The medium used for the culture is not particularly limited, and there can be used a usual medium containing a carbon source, nitrogen source, and inorganic ions as well as organic trace nutrients as required. In the present invention, in particular, a medium containing a significant amount of biotin may be used.

As the carbon source, there can be used saccharides such as glucose, lactose, galactose, fructose and hydrolysate of starch, alcohols such as ethanol and inositol, organic acids such as acetic acid, fumaric acid, citric acid and succinic acid and so forth.

As the nitrogen source, inorganic ammonium salts such as ammonium sulfate, ammonium chloride and ammonium phosphate, organic nitrogen such as soybean hydrolysate, ammonia gas, aqueous ammonia and so forth can be used.

As the inorganic ions or sources thereof, a small amount of potassium phosphate, magnesium sulfate, iron ions, manganese ions and so forth may be added. As a trace amount organic nutrient, it is desirable to add a suitable amount of required substances such as vitamin $B_1$ and yeast extract and so forth as required.

The culture is preferably performed for 16 to 72 hours under an aerobic condition, and the culture temperature is controlled to be 20 to 45° C., and pH to be 5–8.5 during the culture. For adjusting pH, inorganic or organic acidic or alkaline substances, ammonia gas and so forth can be used.

Collection of L-glutamic acid from the culture can usually be carried out by using a combination of known techniques such as techniques using ion exchange resins, precipitation methods and so forth.

BEST MODE FOR CARRYING OUT THE INVENTION

Figure 1:
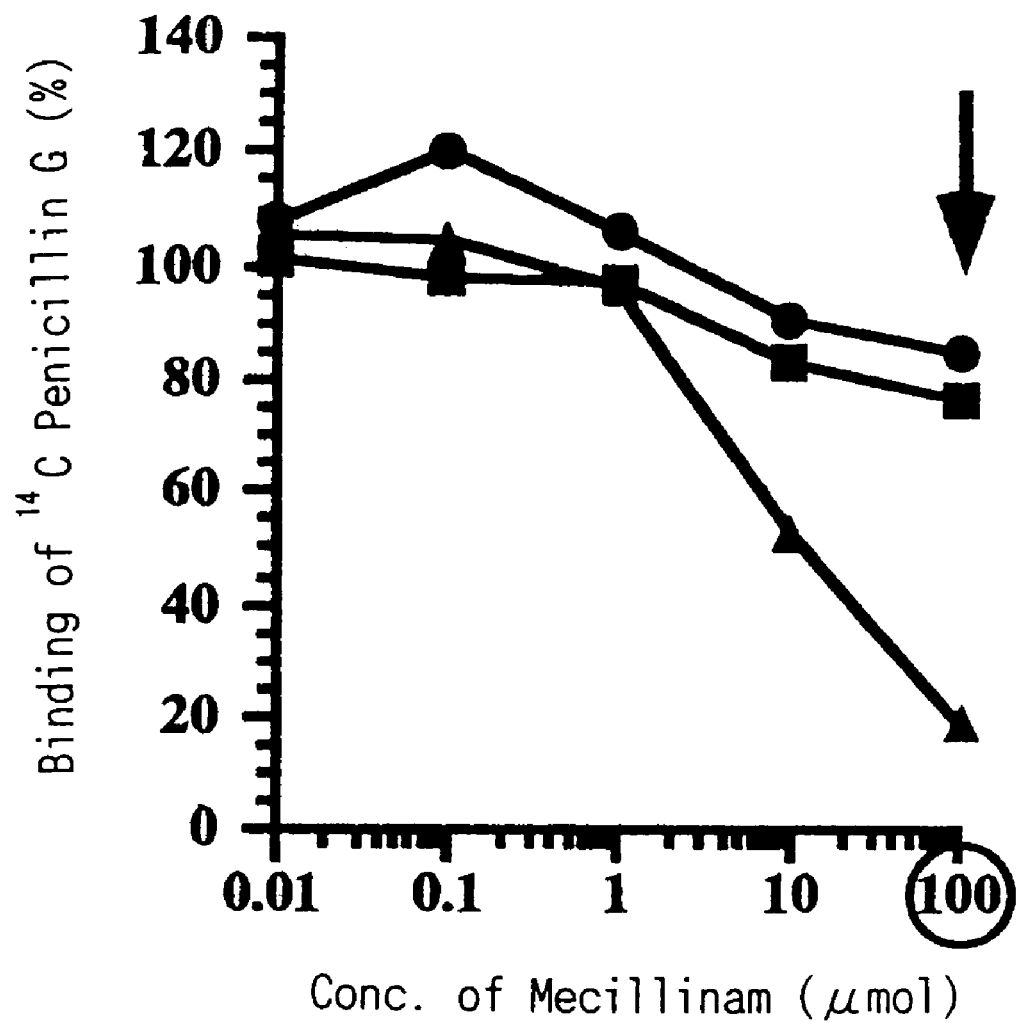
FIG. 1 is a graph showing inhibition by mecillinam for binding of PBP3 and penicillin G. The arrow indicates the minimum inhibitory concentration.

Hereafter, examples of the present invention will be explained.

EXAMPLE 1

Detection of PBP of Coryneform Bacteria

Detection of PBP of coryneform bacteria was performed based on the aforementioned method of Spratt, et al., and specifically as follows.

<1> Preparation of Membrane Fraction

PBP is considered to be a membrane protein. A membrane fraction of a coryneform bacterium was prepared as follows. A wild strain of coryneform bacteria, Brevibacterium lactofermentum ATCC 13869 strain, was inoculated to 20 ml of A medium (containing 10 g of polypeptone, 5 g of yeast extract, 5 g of NaCl and 5 g of glucose in 1 L of water), cultured at 30° C. with shaking, and harvested when the absorption at 660 nm reached about 1.0. The cells were washed in 50 nM sodium phosphate buffer, pH 7.0. Then, the buffer was added with glass beads and sonicated to disrupt the cells. After the disruption debris was removed by centrifugation, the buffer was subjected to ultracentrifugation at 100,000×g for 30 minutes to collect a membrane fraction. The obtained fraction was washed with the same buffer, and the fraction finally suspended in 500 μl of the same buffer was used as the membrane fraction. Protein concentration of this membrane fraction was determined by using a protein quantification kit (produced by PIERCE, Micro BCA Protein assay kit), and found to be 4 mg/ml.

<2> Penicillin Binding Reaction

A volume of 30 μl of the prepared membrane fraction was added with 3 μl of $^{14}$C-penicillin G (produced by Amersham) and allowed to react at 30° C. for 10 minutes. Then, it was added with 2 μl of 15% sarcosyl (sodium N-lauroyl-sarcosine) and 45 mg/ml of penicillin G, and left for 20 minutes at room temperature. Then, the fraction was centrifuged at 13,000 rpm for 30 minutes at 20° C. to obtain a soluble fraction. A sample of this fraction was subjected to SDS-PAGE using gel containing 10% of polyacrylamide, and the gel was fixed, dried and analyzed with an image analyzer BAS2000 produced by Fuji Photo Film Co., Ltd. As a result, three bands were detected at 110 kDa, 100 kDa and 60 kDa, and designated as PBP1, PBP2 and PBP3, respectively.

<3> Analysis Using PBP Binding Inhibitor

Affinity between mecillinam, which is a derivative of penicillin G, and PBP was investigated. The affinity between the derivative and PBP was investigated by adding mecillinam at various concentrations before the aforementioned penicillin binding reaction, and measuring degree of inhibition of the binding with isotope ($^{14}$C) labeled penicillin G. As a result, only PBP3 was inhibited for binding with the labeled penicillin G by the addition of mecillinam. That is, it was clarified that mecillinam should selectively bind to PBP3 (FIG. 1).

EXAMPLE 2

Glutamic Acid Production by Coryneform Bacterium Induced by Addition of Mecillinam The Brevibacterium lactofermentum ATCC 13869 strain was inoculated to the aforementioned A medium, cultured at 30° C. for 2 hours with shaking, then added with 0.01 μM to 100 μM of mecillinam, and further cultured for 8 hours with shaking. Subsequently, glutamic acid concentration in the medium was measured by using Biotech Analyzer AS210 (produced by Asahi Chemical Industry Co., Ltd.) (Table 1).

TABLE 1

| Concentration of added mecillinam (μM) | Concentration of L-glutamic acid (mg/L) |
| --- | --- |
| 0 | 0 |
| 0.1 | 0 |
| 1.0 | 0 |
| 10 | 0 |
| 100 | 575 |

Since it was only PBP3 that bound to mecillinam under the condition where L-glutamic acid production was induced by addition of mecillinam, it was demonstrated that the glutamic acid production induced by the addition of penicillin or mecillinam was caused at least by inhibition of the function of PBP3.

EXAMPLE 3

Cloning of PBP Gene of *Brevibacterium lactofermentum* ATCC 13869

(1) Preparation of chromosomal DNA of *Brevibacterium lactofermentum* ATCC 13869

The *Brevibacterium lactofermentum* ATCC 13869 strain was cultured overnight in 10 ml of L medium (1% of polypeptone, 0.5% of yeast extract, 0.5 g of NaCl, 0.1% of glucose, pH 7.2), and harvested. The cells were washed with 50 mM Tris-HCl, 50 mM EDTA buffer (pH 8.0), and suspended in 800 µl of the same buffer.

To the aforementioned cell suspension, 40 µl of a 50 ml/ml lysozyme solution and 20 µl of a 10 mg/ml ribonuclease solution were added, and the mixture was incubated at 37° C. for 1 hour. The mixture was added with 20 µl of a 20% SDS solution, and incubated at 70° C. for 1 hour. Then, the mixture was added with 24 µl of a 20 mg/ml proteinase K solution, incubated at 50° C. for 1 hour, further added with 24 µl of the proteinase K solution, and incubated for 1 hour.

The cell lysate obtained as described above was added with an equal amount of phenol and stirred. The lysate was left at 4° C. overnight, and then centrifuged to collect an aqueous layer. The aqueous layer was extracted with phenol/chloroform for 2 hours, and with chloroform/isoamyl alcohol for 30 minutes. The extraction was carried out by leaving the lysate after stirring for a predetermined period of time and centrifuging it to collect an aqueous layer. DNA was collected from the obtained extract by ethanol precipitation. The precipitation of DNA was dissolved in 300 µl of TE buffer (10 mM Tris-HCl, 1 mM EDTA, pH 8.0).

(2) Preparation of Chromosomal DNA Library of *Brevibacterium lactofermentum* ATCC 13869

The chromosomal DNA of the *Brevibacterium lactofermentum* ATCC 13869 obtained as described above and a high copy number vector pHSG398 of *Escherichia coli* (Takara Shuzo) were digested by with a restriction enzyme HindIII (Takara Shuzo). These two of DNA were mixed in suitable amounts and ligated by using Takara DNA Ligation Kit ver. 2 (Takara Shuzo) to construct a chromosomal DNA library of *Brevibacterium lactofermentum* ATCC 13869.

(3) Selection of PBP Gene Clone

A murE mutant strain TLK11 of *Escherichia coli* (murE temperature sensitive mutation, J. Bacteriol., 1972, 110: 41–46) was transformed with the chromosomal DNA library of the *Brevibacterium lactofermentum* ATCC 13869 obtained as described above, and cultured at 42° C. overnight on L agar medium (L medium containing 1.5% of agar) containing 20 µg/ml of chloramphenicol.

An emerged colony was inoculated to L liquid medium, and cultured, and plasmid was collected from the obtained cells. As a result, a HindIII fragment of about 5.3 kb was cloned in the plasmid. This plasmid was designated as pHSGH-H.

(4) Determination of Nucleotide Sequence of Cloned DNA Fragment

The aforementioned cloned fragment was subjected to the dideoxy reaction using Thermo Sequenase fluorescent labelled primer cycle sequencing kit with 7-deaza-dGTP (Amersham Pharmacia Biotech) and determined for the nucleotide sequence by using a DNA sequencer DSQ-1000L (Shimadzu). The determined nucleotide sequence is shown as SEQ ID NO: 1.

EXAMPLE 4

Construction of PBP Gene-Disrupted Strain of *Brevibacterium lactofermentum*

A *Brevibacterium lactofermentum* strain with disrupted PBP gene on the chromosome was created by the homologous recombination using the temperature sensitive plasmid disclosed in Japanese Patent Laid-open No. 5-7491.

PCR was performed by using pHSGH-H as a template and oligonucleotides having the nucleotide sequences shown as SEQ ID NOS: 5 and 6 as primers to amplify a PBP gene fragment. The primer shown as SEQ ID NO: 5 contained a sequence corresponding to nucleotide numbers 31–50 of the nucleotide sequence shown as SEQ ID NO: 1, and the primer shown as SEQ ID NO: 6 contained a sequence corresponding to nucleotide numbers 2991–3014 of the nucleotide sequence shown as SEQ ID NO: 1, and each had an EcoRI recognition sequence in the 5' end sequence. The PCR reaction was carried out by using a commercially available PCR apparatus (DNA Thermal Cycler Model PJ2000 produced by Takara Shuzo etc.), and TaqDNA Polymerase (Takara Shuzo) according to the manufacturer's protocol.

The obtained amplified fragment was treated with EcoRI, and inserted into the EcoRI site of pHSG299 (produced by Takara Shuzo) to produce pHSGE. Separately, the temperature sensitive plasmid for coryneform bacteria, pHSC4, was digested with BamHI and KpnI to obtain a gene fragment containing a replication control region, and the obtained fragment was blunt-ended by using Blunting kit produced by Takara Shuzo, and inserted into the XbaI site of pHSGE using a XbaI linker (produced by Takara Shuzo) to produce pHSGX. Then, pHSGX was digested with BamHI and KpnI, blunt-ended by using Blunting kit produced by Takara Shuzo and allowed to cause self-ligation by using Takara DNA Ligation Kit ver. 2 (Takara Shuzo). The obtained plasmid pHSGXΔBK had an internal deletion of the PBP gene.

By using the plasmid pHSGXΔBK for PBP gene substitution obtained as described above, gene substitution between a deletion type PBP gene and a PBP gene on chromosomal DNA of *Brevibacterium lactofermentum* was performed by the double recombination technique. Specifically, it was attained as follows. The *Brevibacterium lactofermentum* ATCC 13869 was transformed with pHSGXΔBK by the electric pulse method (see Japanese Patent Laid-open No. 2-207791). The transformant was cultured at 25° C. for 6 hours in M-CM2G liquid medium with shaking and inoculated on M-CM2G medium containing 25 µg/ml of kanamycin. A strain that formed a colony at 34° C. was obtained.

In the obtained strain, the deletion type PBP gene was recombined with the PBP gene originally present on the chromosome, and the two fusion genes of the chromosomal PBP gene and the deletion type PBP gene are inserted into the chromosome so that the other portions of the recombinant DNA (vector segment, temperature sensitive replication control region and drug resistance marker) should be present between the two fusion genes. Therefore, the transformant strain could grow at a high temperature because the normal PBP gene was dominant in this state.

Then, the transformant strain was cultured at 25° C., and a strain in which the PBP gene on the chromosome was replaced with the deletion type gene was selected from the strains that could grow at 25° C. but could not grow at 34° C., and designated as ΔP3/p3 strain. In the ΔP3/p3 strain, the deletion type PBP gene was left on the chromosomal DNA, and a plasmid containing a normal PBP gene was present in the cell. It was confirmed if the PBP gene on the chromosome was replaced with the deletion type by determining the nucleotide sequence of the ligation region left behind the deleted region.

INDUSTRIAL APPLICABILITY

According to the present invention, a gene coding for a penicillin binding protein (PBP gene) of a coryneform bacterium is provided. By using a coryneform bacterium of which PBP gene on the chromosome was disrupted with the gene, L-glutamic acid can be produced in the presence of a significant amount of biotin without adding a biotin activity suppressor.

The invention claimed is:

1. An isolated DNA, wherein said DNA is defined in the following (a) or (b):
   (a) a DNA which comprises nucleotides 881 to 2623 of SEQ ID NO:1;
   (b) a DNA which is hybridizable with a nucleotide sequence comprising at least nucleotides 881 to 2623 of SEQ ID NO:1 under a stringent condition, which comprises washing at 60° C. in 1×SSC and 0.1% SDS, and wherein said DNA codes for a protein having the ability to bind to penicillin.

2. An isolated DNA which codes for a protein which has the amino acid sequence of SEQ ID NO:2.

3. The DNA of claim 1, which is (a).

4. A vector comprising the DNA of claim 1.

5. A vector comprising the DNA of claim 2.

6. A vector comprising the DNA of claim 3.

7. A bacterial cell selected from the group consisting of *Escherichia coli* and a coryneform bacterium, comprising the vector of claim 4.

8. A bacterial cell selected from the group consisting of *Escherichia coli* and a coryneform bacterium comprising the vector of claim 5.

9. A bacterial cell selected from the group consisting of *Escherichia coli* and a coryneform bacterium comprising the vector of claim 6.

10. A method for producing L-glutamic acid comprising:
   a) deleting all or a portion of a gene encoding an endogenous penicillin binding protein 3 (PBP3) in a coryneform bacterium such that the activity of endogenous PBP3 is eliminated;
   b) transforming said coryneform bacterium with a plasmid containing a temperature sensitive replicon and a DNA encoding a functioning PBP3;

c) cultivating said coryneform bacterium in a liquid medium to produce and accumulate L-glutamic acid; and d) collecting the L-glutamic acid;

wherein said DNA comprises nucleotides 881 to 2623 of SEQ ID NO:1 or a DNA hybridizable thereto under stringent conditions which include washing in 1×SSC and 0.1% SDS at 60° C.

11. The method according to claim 10, wherein said cultivating comprises growing the coryneform bacterium at a first temperature to proliferate the coryneform bacterium, and subsequently incubating the coryneform bacterium at a second temperature to produce L-glutamic acid, wherein the functioning PBP3 encoded by the DNA on the plasmid is produced at the first temperature, and the PBP3 encoded by the DNA on the plasmid is not produced at the second temperature because the expression of the functioning PBP3 is under the control of the temperature sensitive replicon.

12. The method according to claim 10, wherein the functioning PBP3 has the amino acid sequence shown in SEQ ID NO:2.

13. The method according to claim 10, wherein said functioning PBP3 is encoded by a DNA which comprises nucleotides 881 to 2623 of SEQ ID NO:1.

14. The method according to claim 10, wherein said endogenous PBP3 gene comprises nucleotides 881 to 2623 of SEQ ID NO:1 or a DNA hybridizable thereto under stringent conditions.

15. The method according to claim 14, wherein said endogenous PBP3 gene comprises nucleotides 881 to 2623 of SEQ ID NO:1.

16. In a method of making a seasoning, the improvement comprising producing L-glutamic acid according to the method according to claim 10.

17. In a method of making a seasoning, the improvement comprising producing L-glutamic acid according to the method according to claim 11.

18. In a method of making a seasoning, the improvement comprising producing L-glutamic acid according to the method according to claim 12.

19. In a method of making a seasoning, the improvement comprising producing L-glutamic acid according to the method according to claim 14.

20. In a method of making a seasoning, the improvement comprising producing L-glutamic acid according to the method according to claim 13.

21. In a method of making a seasoning, the improvement comprising producing L-glutamic acid according to the method according to claim 15.

* * * * *